(12) United States Patent
Funch-Nielsen

(10) Patent No.: US 12,186,071 B2
(45) Date of Patent: Jan. 7, 2025

(54) DEVICE TO MEASURE BREATH HUMIDITY

(71) Applicant: EXHALATION TECHNOLOGY LIMITED, Cambridge (GB)

(72) Inventor: Helle Funch-Nielsen, Horsholm (DK)

(73) Assignee: EXHALATION TECHNOLOGY LIMITED, Cambridge (GB)

( * ) Notice: Subject to any disclaimer, the term of this patent is extended or adjusted under 35 U.S.C. 154(b) by 815 days.

(21) Appl. No.: 17/293,727

(22) PCT Filed: Nov. 14, 2019

(86) PCT No.: PCT/GB2019/053225
§ 371 (c)(1),
(2) Date: May 13, 2021

(87) PCT Pub. No.: WO2020/099874
PCT Pub. Date: May 22, 2020

(65) Prior Publication Data
US 2022/0007961 A1    Jan. 13, 2022

(30) Foreign Application Priority Data

Nov. 14, 2018 (GB) .................................. 1818584

(51) Int. Cl.
*A61B 5/08* (2006.01)
*A61B 5/087* (2006.01)
(Continued)

(52) U.S. Cl.
CPC .............. *A61B 5/082* (2013.01); *A61B 5/087* (2013.01); *A61B 5/097* (2013.01); *G01N 33/497* (2013.01);
(Continued)

(58) Field of Classification Search
CPC ...... A61B 5/08–097; A61B 2560/0425; A61B 2562/0219; A61B 2562/029;
(Continued)

(56) References Cited

U.S. PATENT DOCUMENTS 8,607,794 B2 * 12/2013 Varga ..................... A61M 16/00
128/207.18
10,850,050 B2 * 12/2020 Alizoti .............. A61M 15/0086
(Continued)

FOREIGN PATENT DOCUMENTS

CN    208770598 U  *  4/2019
DE        19951204        8/2002
(Continued)

OTHER PUBLICATIONS

English Translation of CN 208770598 U, Orange Technology (tianjin) Co Ltd, 5 pages, printed on Mar. 5, 2024. (Year: 2019).*
(Continued)

*Primary Examiner* — Matthew Kremer
*Assistant Examiner* — Jennifer Grace Baires-Tweed
(74) *Attorney, Agent, or Firm* — Renner, Otto, Boisselle & Sklar, LLP.

(57) ABSTRACT

The device as disclosed herein is to measure breath humidity, the device comprises an inlet fluidly connected at a first end of a tubular body, said tubular body defining an inner tube volume. The device further comprises a condenser plate, fluidly connected to the second end of the tubular body to receive exhaled breath. A partition wall intermediate the first and second ends divides the inner tube volume into first and second chambers, the second chamber providing fluid access to the condenser plate. The wall has a one-way valve therethrough allowing breath from the first to the second chamber. The device further comprises one or more apertures in the tubular body wall of the first chamber, the or
(Continued)

each aperture fluidly linking a sensor to the first chamber, and a relative humidity sensor fluidly linked to the second chamber.

13 Claims, 12 Drawing Sheets

(51) Int. Cl.
 *A61B 5/097* (2006.01)
 *G01N 33/497* (2006.01)
(52) U.S. Cl.
 CPC ............... *A61B 2560/0425* (2013.01); *A61B 2562/0219* (2013.01); *A61B 2562/029* (2013.01); *G01N 33/4975* (2024.05)
(58) Field of Classification Search
 CPC .... A61B 2560/0214; A61B 2560/0443; A61B 2562/18; G01N 33/497; G01N 2033/4975–4977
 See application file for complete search history.

(56) References Cited

U.S. PATENT DOCUMENTS

| | | | |
|---|---|---|---|
| 2007/0073183 A1 | 3/2007 | Kline | |
| 2008/0283062 A1* | 11/2008 | Esposito, Jr. | ..... A61M 16/0051 128/204.22 |
| 2010/0268106 A1 | 10/2010 | Johnson | |
| 2017/0360328 A1 | 12/2017 | Otrea | |
| 2018/0056302 A1 | 3/2018 | Ahmad et al. | |
| 2019/0254538 A1* | 8/2019 | Erdman | ............... A61B 5/6803 |

FOREIGN PATENT DOCUMENTS

| | | | | |
|---|---|---|---|---|
| EP | 2173250 | | 8/2016 | |
| EP | 2173250 B1 | * | 8/2016 | ............ A61B 5/097 |
| GB | 2506863 A | * | 4/2014 | ............ A61B 5/082 |
| WO | WO-2005117701 A1 | * | 12/2005 | .......... A61B 5/0833 |
| WO | 2009/013450 A1 | | 1/2009 | |
| WO | WO-2010110051 A1 | * | 9/2010 | ......... G01N 33/0031 |
| WO | WO-2014132077 A1 | * | 9/2014 | ......... G01N 33/0059 |
| WO | WO-2017079425 A1 | * | 5/2017 | |
| WO | 2018/061022 A1 | | 4/2018 | |
| WO | 2018/101650 A1 | | 6/2018 | |

OTHER PUBLICATIONS

English Translation of WO 2010110051 A1, Sharp Corporation, 28 pages, printed on Mar. 5, 2024. (Year: 2010).*
International Search Report and Written Opinion for International Application No. PCT/GB2019/053225 mailed Feb. 5, 2020.

* cited by examiner

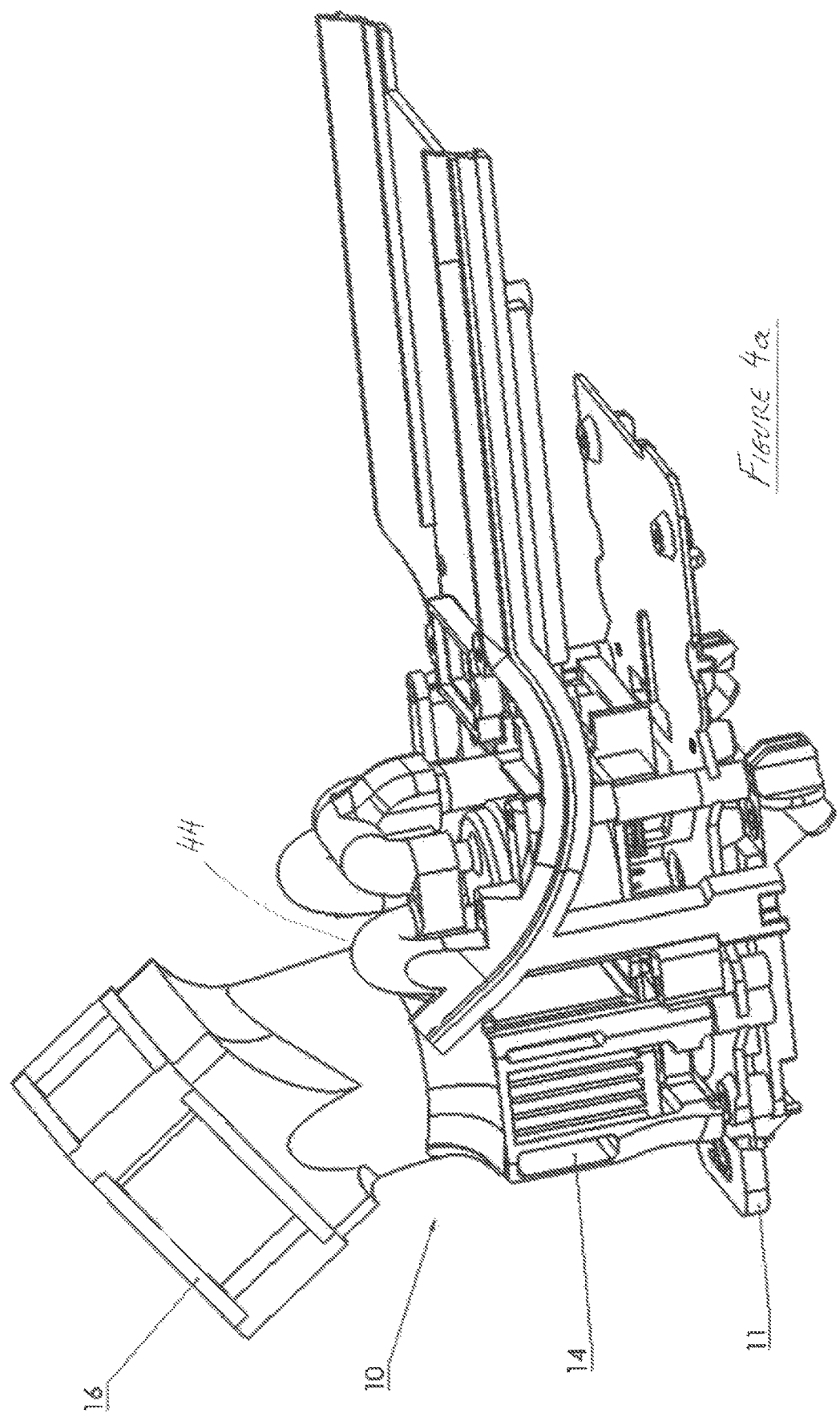

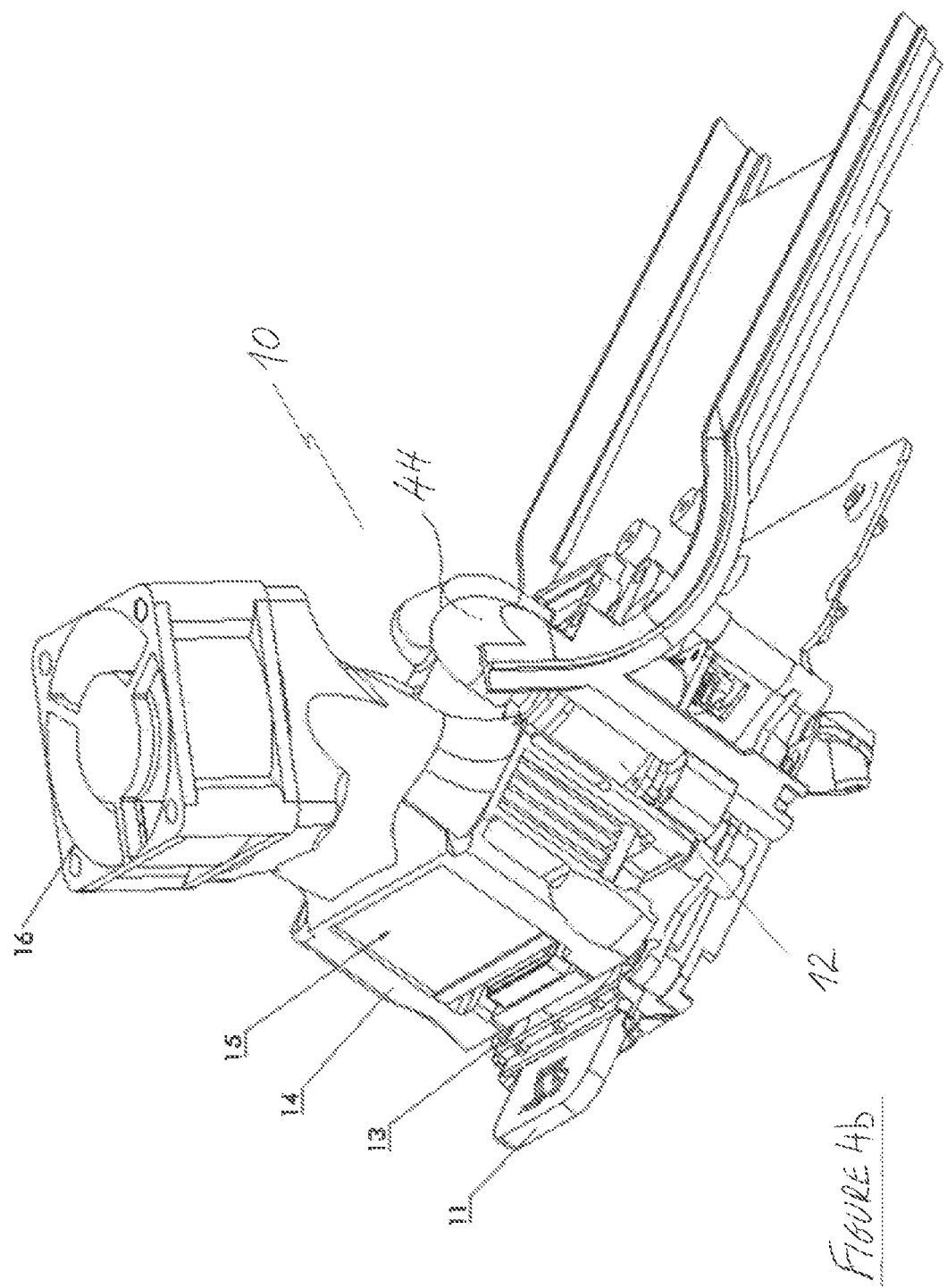

DEVICE TO MEASURE BREATH HUMIDITY

This application is a national phase of International Application No. PCT/GB2019/053225 filed Nov. 14, 2019, which claims priority to United Kingdom Application No. 1818584.3 filed Nov. 14, 2018, all of which are hereby incorporated herein by reference in their entireties.

FIELD OF THE INVENTION

The present invention concerns a device for measuring breath humidity and in particular a device which can also measure other parameters, the breath humidity measurement to be used alone or in conjunction with other parameters, the measurements to be used in the identification, triaging and longitudinal tracking of diseases including lung diseases.

BACKGROUND TO THE INVENTION

The present invention relates to a device for measuring breath humidity and the use of the measurement for the determination of disease states, especially that of human conditions, but including animals such as horses, dogs, etc.

The measurement of breath humidity can be used for the identification, triaging and longitudinal tracking of diseases including lung diseases. Further, combining a measurement of breath humidity with a number of other breath parameters can increase clinical accuracy when triaging patients or tracking patients' medical conditions.

The invention is particularly for use in exhaled breath and in part determines the relative amounts of exhaled breath from alveolar, central and what has been traditionally known as the lung's dead volumes. The exhaled breath humidity can be expressed in absolute and/or relative terms, and can be used as standalone measurement or used in conjunction with several other exhaled breath parameters including: measurements on the exhaled breath condensate, measurements upon the exhaled breath gas phase, measurement of constituents within the exhaled breath vapour phase and/or gas phase, breath volume, exhalation rate, forced air manoeuvres, breath temperature etc. Examples of gas and vapour phase constituents or properties of those constituents that can be measured in conjunction with breath humidity include: pH, sugars, glucose, ketones, cations, anions, and small molecules such as nitric oxide, hydrogen peroxide, oxygen, carbon dioxide, carbon monoxide etc. Additionally, "markers" of other disease states such as cancer can also be determined.

The measurement of breath humidity can be measured in parallel or sequentially with other breath parameters, either in a combination device or using separate devices.

Within a healthy population the measurement of breath humidity is an indicator of a person's total body water content and can be used as an indicator of a person's hydration level. The breath humidity value can be used in isolation, compared or combined with other breath parameters for more accurate clinical decisions.

In a previous application, EP2173250, in the name of the current Applicant, a device is described which allows efficient collection of exhaled breath, and in particular collection with a minimal loss of volatile components, which would introduce error into subsequent analyses. Once the breath sample is condensed, it is then made available for analysis. However, the device is not able to measure the humidity of the breath and the clinical usefulness of knowing the patient's breath humidity is lost to the patient and the clinician if this device is used.

Prior art document DE199 51 204 describes a method of condensing exhaled breath until a predetermined volume of sample is obtained, but again without knowing the breath humidity there is no way of knowing how long a patient will take to provide an adequate volume of condensate. Knowing parameters such as breath temperature, breath flow rate along with breath humidity, the time necessary to collect a volume of exhaled breath condensate can be calculated which avoids the use of an arbitrary setpoint based on time, number of breaths etc. When filling a breath condensate collection device, it is not untypical to fail to fill the device in a reasonable amount of time; this is because unbeknownst to the clinician or patient the patient has a low humidity on the breath and is simply not passing enough vapour, which is subsequently condensed, to fill the device. These subjects may be termed "dry breathers".

Though a search has been made for prior art documents describing our invention none has been found, documents considered include: WO2018061022A1, WO2018101650A1, US2017/360328 and US2018/056302.

WO2018061022A1—This application discloses a lung condition monitoring device where CdS nanoparticles are used as part of humidity sensing for performing ultrafast detection of humidity level of a human while breathing out.

WO2018101650A1—The disclosed invention relates to a method and an apparatus for analysing biogas contained within a single breath, and to subsequently monitor the respiratory diseases of a patient through the analysed biogas.

US2017/360328—The device disclosed in this document measures the moisture content of a single breath or of multiple breaths using two electrodes: one working electrode functioning by cationic exchange with water (e.g. utilising a perfluorocarbon), and a reference electrode which is protected from the exhaled breath by a cover.

US2018/056302—The device here measures a first breath feature (such as humidity) and a second feature such as a specific analyte which, in the exemplified embodiment is a ketone. The latter measurement is obtained utilising nanoparticle-based sensor.

Patients can have different breath humidity levels, for example a group of Healthy Controls has a higher relative breath humidity than a group of patients with chronic obstructive pulmonary disease (COPD), but the breath humidity is often an unknown and therefore an uncontrolled parameter when making breath measurements on these COPD patients.

When measuring constituents of the breath within the gas phase such as carbon monoxide, carbon dioxide, nitric oxide, etc., it is common to pass the air through filters, scrubbers, dehumidifiers etc. to deliberately remove fractions of the breath including the water vapour. This process may also be carried out without knowledge and therefore the removal may be 'accidental'. These devices then report the concentration of a molecule in the dried and/or processed breath sample. This is not necessarily the same as the concentration of the molecule in the initial exhaled breath, but it is often reported and interpreted as such. The true concentration of analytes in the breath is in part influenced by the humidity and temperature of the breath and the partitioning of molecules between the gas phase and the vapour phase, which in part is specific to each type of molecule. By measuring the breath humidity, one can normalise the concentration of analytes measured on the breath relative to the breath humidity and therefore reduce an otherwise uncontrolled or unknown patient-to-patient variable, therefore increasing the clinical accuracy.

Currently, researchers and clinicians are interested in measuring parameters of the breath and/or analytes upon the breath as part of disease identification, triaging or longitudinal monitoring. A parameter not currently used is breath humidity. Currently, with COPD patients their diagnosis and evaluation of care may be performed by a series of tests including: forced air movements, fractionated nitric oxide measurements (FNO), clinical questionnaires and exhaled breath condensate (EBC) hydrogen peroxide measurements, but the measurement of exhaled breath humidity is not routinely measured.

SUMMARY OF THE INVENTION

According to a first aspect of the invention, there is provided a device to measure breath humidity, the device comprising a tubular body, said tubular body defining an inner tube volume, an inlet fluidly connected to the inner tube volume;

a condenser plate, fluidly connected to the second end of the tubular body to receive exhaled breath;

a partition wall intermediate the first and second ends and dividing the inner tube volume into first and second chambers, the second chamber providing fluid access to the condenser plate;

the partition wall having a one-way valve therethrough allowing breath from the first to the second chamber;

the device further comprising one or more apertures in the tubular body wall of the first chamber, the or each aperture fluidly linking a sensor to the first chamber, a relative humidity sensor fluidly linked to the second chamber.

Preferably, the or each sensor is linked to a data storage device to enable data to be transmitted quickly to a health care specialist or to be analysed.

Optionally, a sensor is a $CO_2$ sensor.

Optionally a sensor is an air-flow sensor, to aid in determining if the device is being used correctly.

Optionally a sensor is able to detect hydrogen peroxide to enable diagnosis of a respiratory problem.

Preferably, the or each sensor is housed in a demountable housing, attachable to the device to allow for easy replacement so that the device can be used by a subsequent patient or replaced if faulty.

Preferably, the condenser plate is cooled by a Peltier piece type cooling means. Further preferably, a heater plate is housed in cooling arrangement with the Peltier piece to aid in the rapid removal of heat energy from the condenser plate. The device yet further preferably includes a fan to draw air across the heater plate to remove heat energy from the device.

The device preferably includes an accelerometer to determine whether the device is being held steadily to ensure proper functioning of the elements of the device carrying out the analysis.

The second chamber preferably has a fluid outlet to discharge breath from the device and minimise any turbulent flow.

The second chamber preferably includes a directing means, which is further preferably a ramp, to direct breath entering the second chamber onto the condenser plate.

BRIEF DESCRIPTION OF THE DRAWINGS

The invention is described with respect to the attached drawings which show, by way of example only, two embodiments of a device to measure breath humidity and other parameters. In the drawings:

FIGS. 4a, and 4b are images of a device;

DETAILED DESCRIPTION OF THE INVENTION

A person's breath humidity is a means by which it can be established that a person is ill. Furthermore, breath humidity can be used to differentiate people within an illness category, for example COPD patients can be separated from Asthma patients. This is illustrated in FIG. 1 below.

Figure 1:
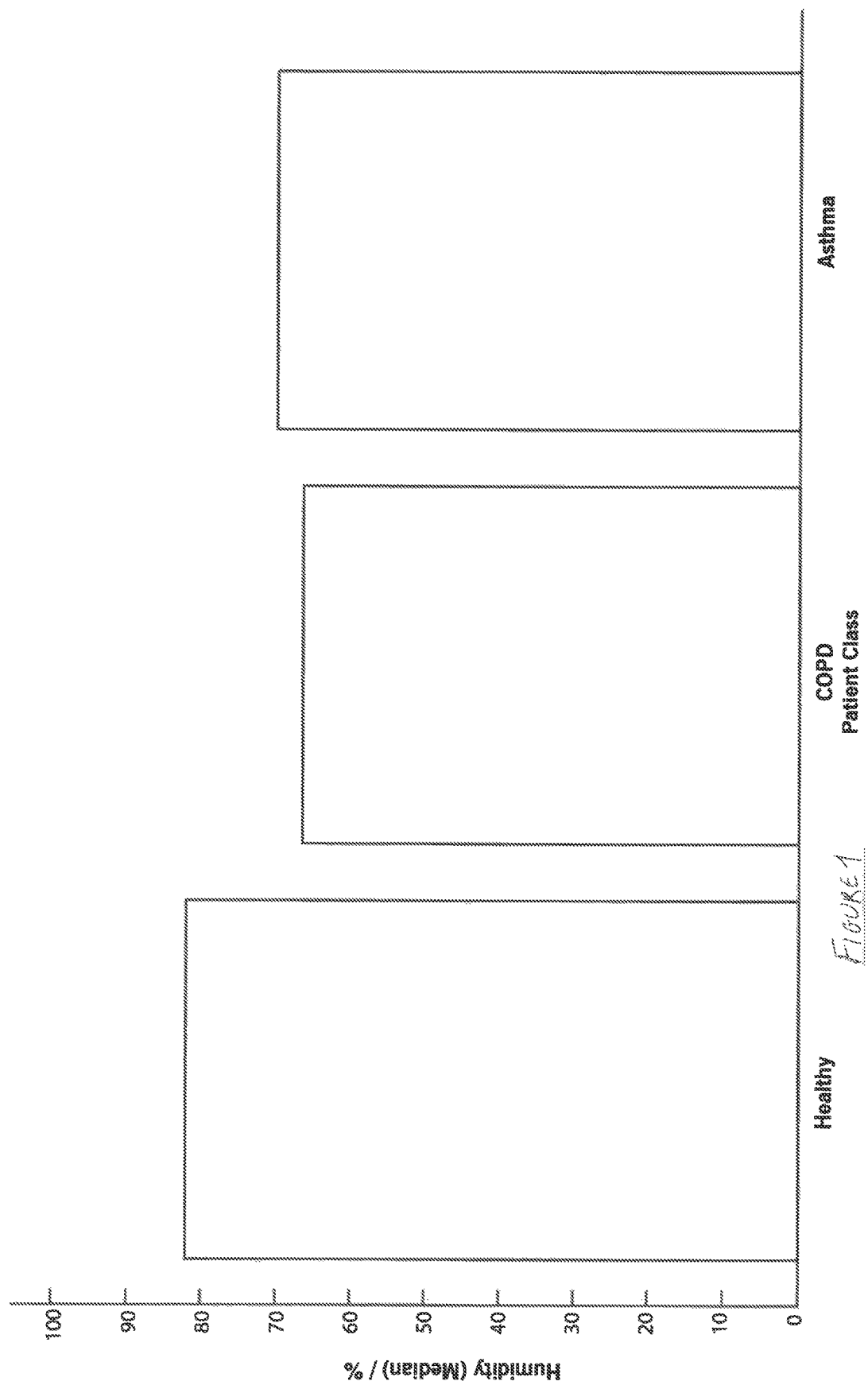
FIG. 1 illustrates breath humidity of patients having different respiratory conditions.

In FIG. 1 the average relative humidity (RH) measured of breath samples of a COPD patient group was approximately 15% lower than the relative humidity measured on the healthy patient group. In simple terms, the COPD patients generally had less water vapour on their breath relative to the Healthy Control Group. Further it can be seen that the Asthma group has an average breath relative humidity between those of the Healthy Control Group and the COPD Group. The data in FIG. 1 is taken from over 155 individuals and indicates that it would be possible to diagnose or triage between COPD, Asthma and Healthy controls from the breath relative humidity. Importantly breath humidity becomes more useful only when combined with other parameters such as forced air movement, exhaled breath condensate hydrogen peroxide and fractionated nitric oxide (FNO).

Figure 2:
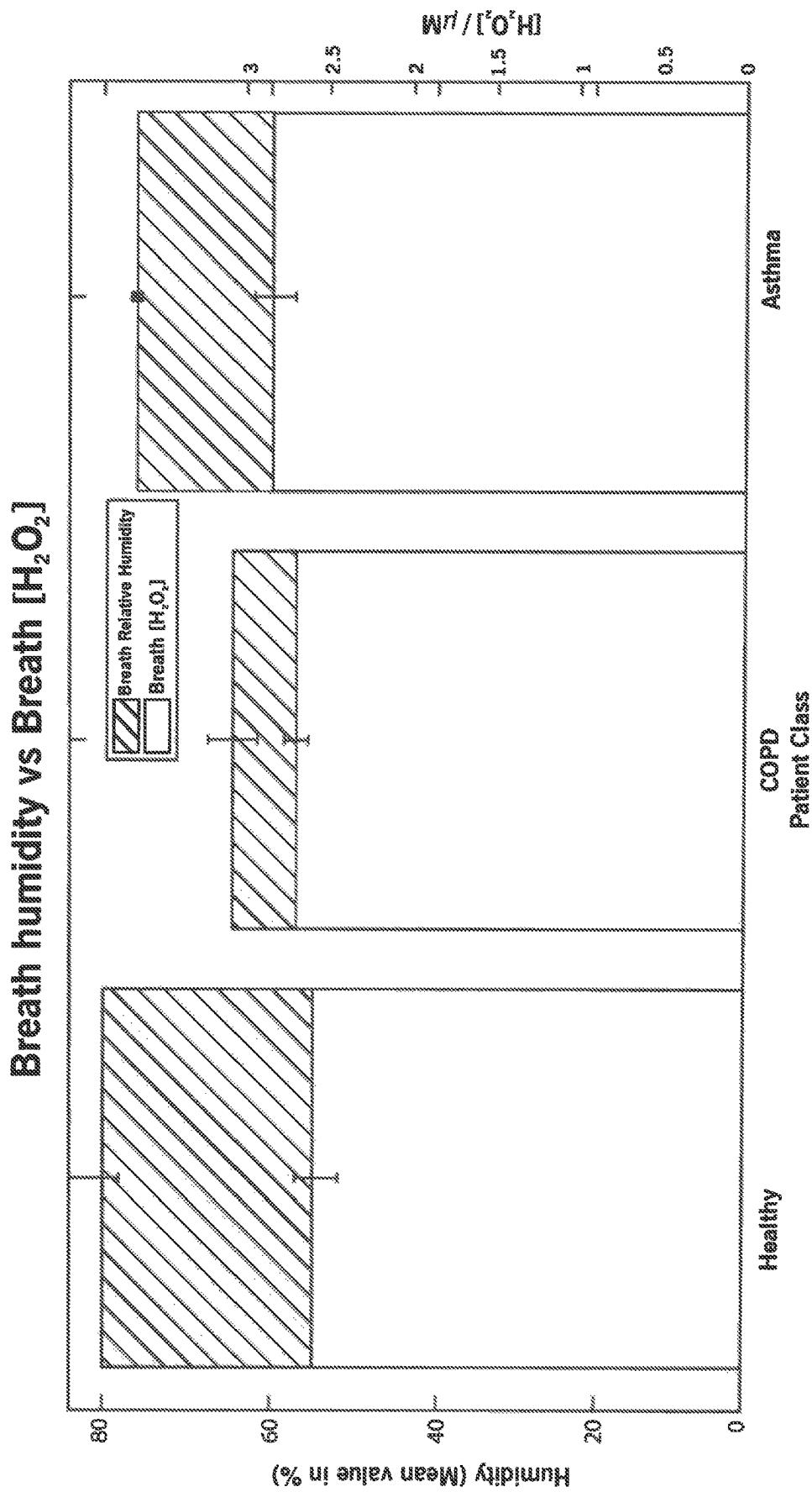
FIG. 2 illustrates combining measured breath humidity and hydrogen peroxide values.

The data in FIG. 1 indicates that breath humidity is sufficient by itself to classify a person as healthy or with lung disease but sub-classifying whether a patient is for example COPD or Asthma is more problematic as the approximate difference in average relative breath humidity is 5%. If the breath humidity were combined with a second parameter, then it would be possible to categorise the patients into further groups such as COPD and Asthma. For example, if the exhaled breath RH is examined alongside the exhaled breath condensate (EBC) hydrogen peroxide concentration then there is a clear pattern of COPD patients having the intermediate value of EBC hydrogen peroxide concentration and the lowest RH, whereas the healthy group has the lowest EBC hydrogen peroxide concentration and the highest breath RH. The asthma group has the intermediate value on RH and the highest value on the EBC hydrogen peroxide concentration (see FIG. 2).

As discussed, two, three or more breath parameter can be combined to provide a score or scale which better classifies a patient, for example if EBC hydrogen peroxide concentration is divided by relative humidity then the difference between the asthma and COPD group is amplified (see Table 1)

TABLE 1

| Approximate average EBC hydrogen peroxide (µM) | Breath RH (%) | Helle Score (EBC hydrogen peroxide/breath RH) |
|---|---|---|
| 2.6 | 0.8 | 3.25 |
| 2.7 | 0.78 | 3.46 |
| 2.8 | 0.65 | 4.31 |

The combining of EBC hydrogen peroxide with RH clearly leads to a score, which is termed herein as the Helle Score, which offers an enhanced separation of asthma patients from COPD patients. The combination of breath humidity is not limited to that with hydrogen peroxide and additional clinical benefits can be expected by combining FNO, pH etc. with breath humidity. The combining can be carried out by a processor (not illustrated) included in the device, or remotely.

Similarly, by combining the output from a clinical questionnaire with breath humidity a clinically useful score or scale can be generated. Creating a score or scale by breath measurement and breath humidity is not limited to simple mathematical operations and other operators include powers, logarithms, trigonometric functions etc. can also be used separately or in combination.

To measure a patient's breath humidity a device is needed having a number of functions, including: the device must be able to engage with the patient's mouth, the device must be able to guide the exhaled breath along a determined path, the device must be able to minimise dead space between the mouth and the breath collection zone the device must be able to measure humidity, the device must be able to protect the humidity sensor from non-respiratory vapour and aerosol, the device must shield the humidity sensor from the ambient conditions including the ambient vapour, the device must be able to measure vapour whose only source was the respiratory system, optimally the device should also measure breath temperature, the device should act so that an exhalation displaces the air from the device remaining from the previous exhalation.

Figure 3:
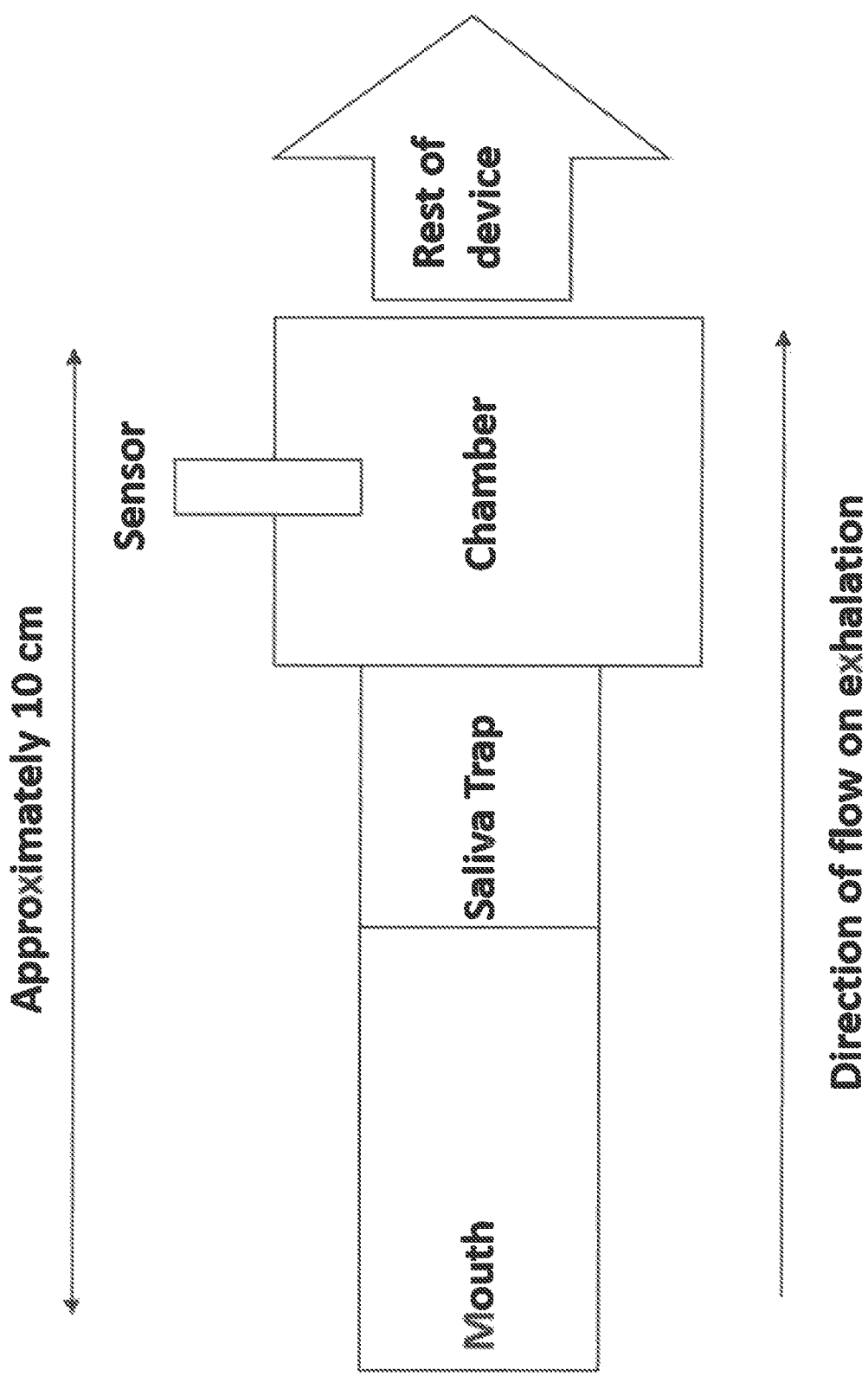
FIG. 3 illustrates air-flow in a device.

A major source of potential contamination to any measurement of breath humidity is the ambient humidity within the vicinity of the patients under test, and so the breath humidity should be made using an enclosed device, where the sensor is shielded from the ambient humidity. Further the humidity sensor should be in close proximity to the mouth, approximately 10 cm, and the sensor should be protected from contamination such as saliva aerosol originating in the mouth as opposed to the airways (see FIG. 3).

FIGS. 4a, 4b are images of a hand-held embodiment of a device 10, able to measure breath humidity and carbon dioxide levels as well as a number of other parameters. In these figures, a replaceable cartridge 11 is shown which incorporates a microfluidic analysis system allowing determination therein of, for example, hydrogen peroxide, pH, glucose, ketones, nitrogen oxides etc. The cartridge 11, detailed in FIG. 7, can include a collection element such as a cooled dish, as disclosed in published patent application WO2009013450 to the same applicant, to collect a portion of the breath, typically the alveolar portion.

The device 10 additionally includes a $CO_2$ sensor 12, which is for example a near-infrared sensor. A condenser plate 13 is located adjacent a Peltier piece 14 which provides cooling to the plate 13. Located to the other side of the Peltier piece 14 is a heat plate 15 which acts as a heat sink for the Peltier piece 14. A fan 16 acts to draw unwanted heat from the device 10, in particular passing air across the heat plate 15 to cool the heat plate 15 down.

Figure 5:
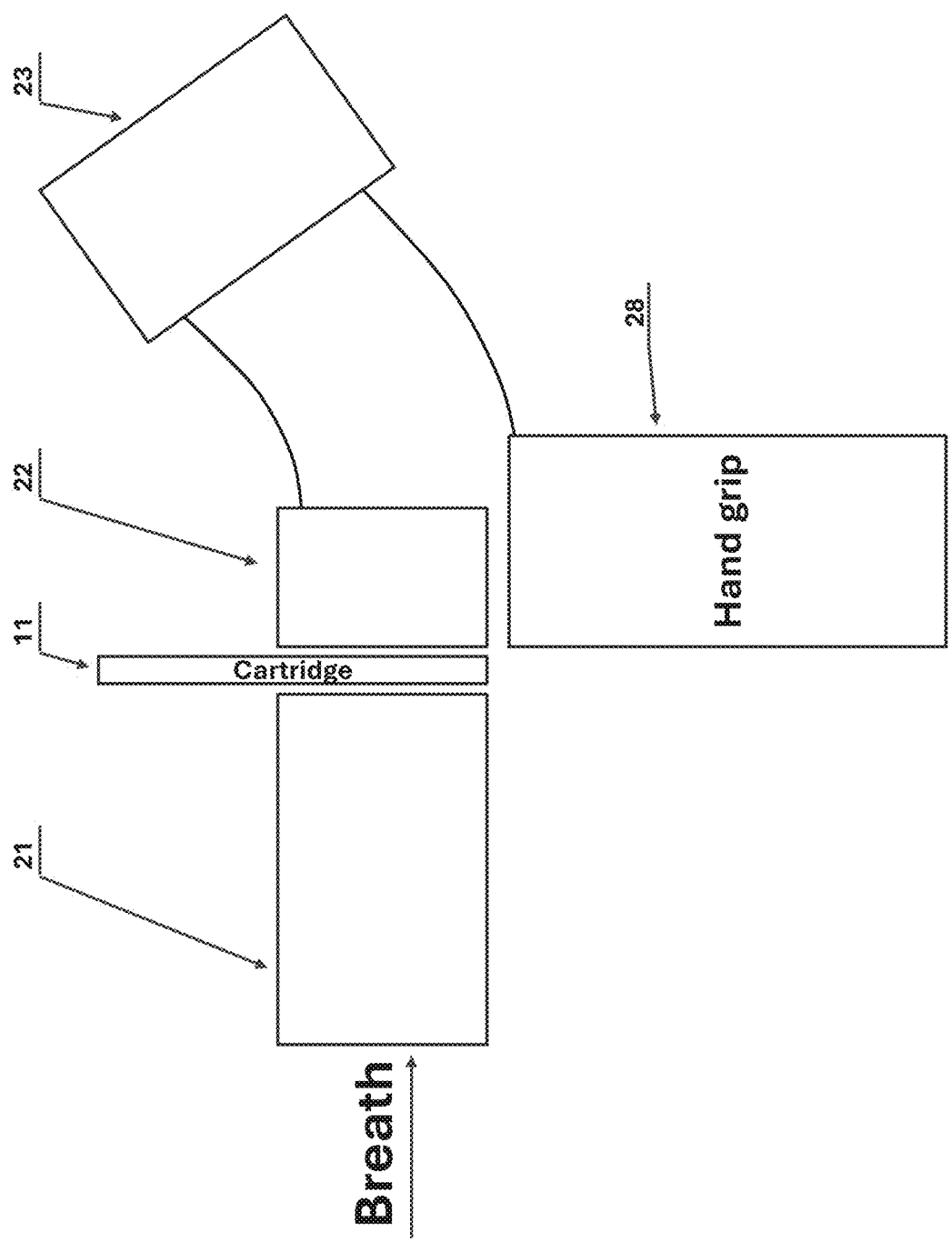
FIG. 5 is a diagrammatic illustration of a device.

FIG. 5 illustrates schematically, a device 20 in accordance with the invention. The device 20 has an air-inlet 21 which is designed to facilitate a user breathing into the device 20. Typically, therefore, the inlet 21 is profiled to enable a user to ensure that the majority of an exhaled breath enters the device 20. The inlet 21 can include or be coupled to a replaceable mouthpiece to improve hygiene between different users of the device 20.

The inlet 21 opens onto the cartridge 11 and also allows a portion of the exhaled breath to be partitioned into a separate flow stream which is then led to sensors incorporated into the device 20 itself, for example a $CO_2$ sensor. The sensors are located within the housing 22. The unused breath is provided with an exit 23 to prevent unwanted turbulent flow or back flow of breath. A hand-grip 28 is provided to enable a user to hold the device 20 in a position convenient to comfortably exhale. The hand-grip 28 can be absent where the device 20 is to be used as a desk-top device within a health facility or otherwise. In a further option a device may include a demountable handle-grip giving flexibility in use, of the device.

Figure 6:
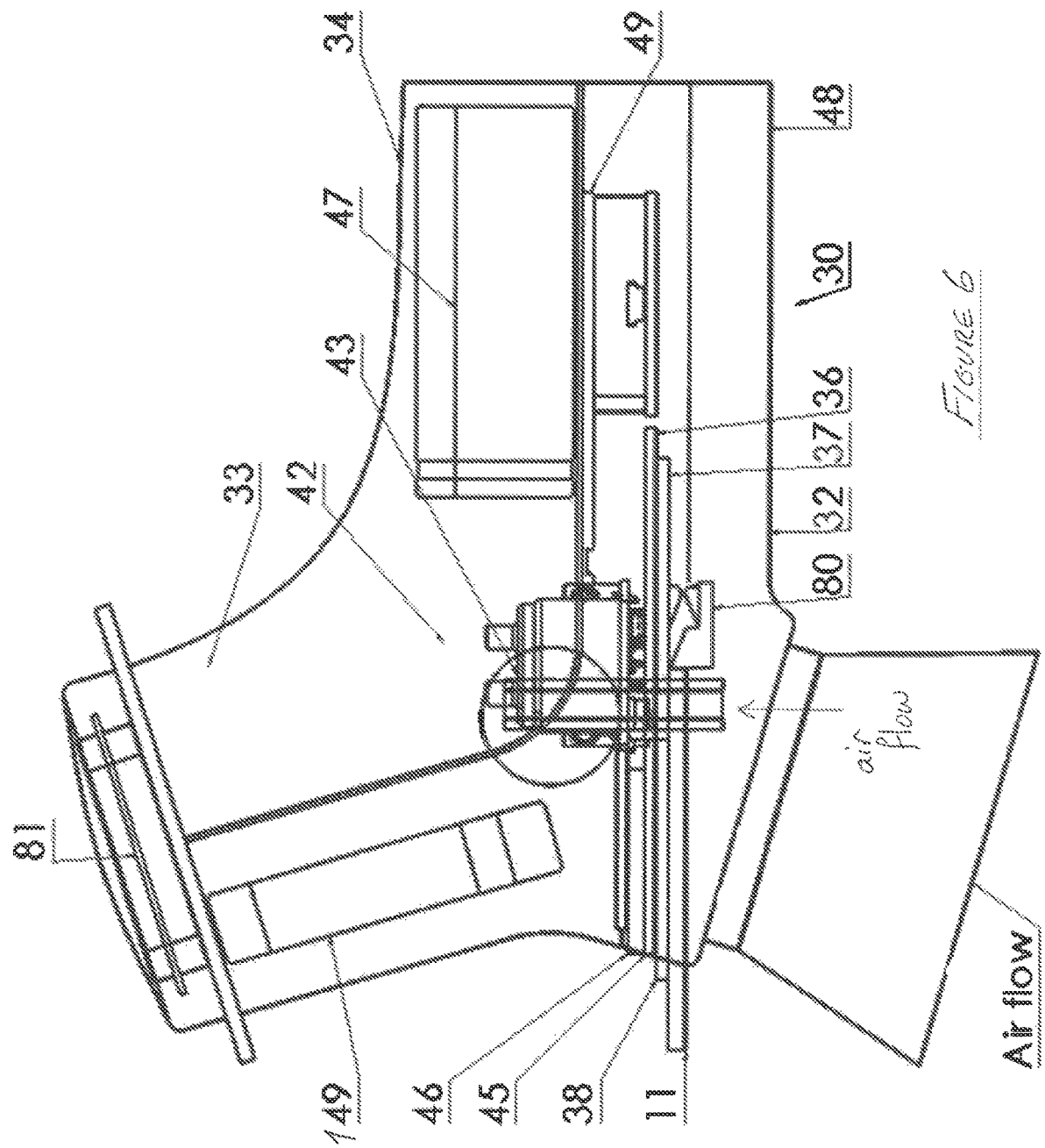
FIG. 6 illustrates the internal way out of a device.

FIG. 6 illustrates the internal features of a device 30 in accordance with an embodiment of the invention. The device 30 has a breath inlet 31 and a handle 34 allowing a user to hold the device 30. In this embodiment the handle 34 is integrally formed with other elements of the device 30, such as with the outlet 33 and the housing 32. The outer surface of the handle 34 can be ergonomically profiled to facilitate a user in gripping the device.

Figure 7A:
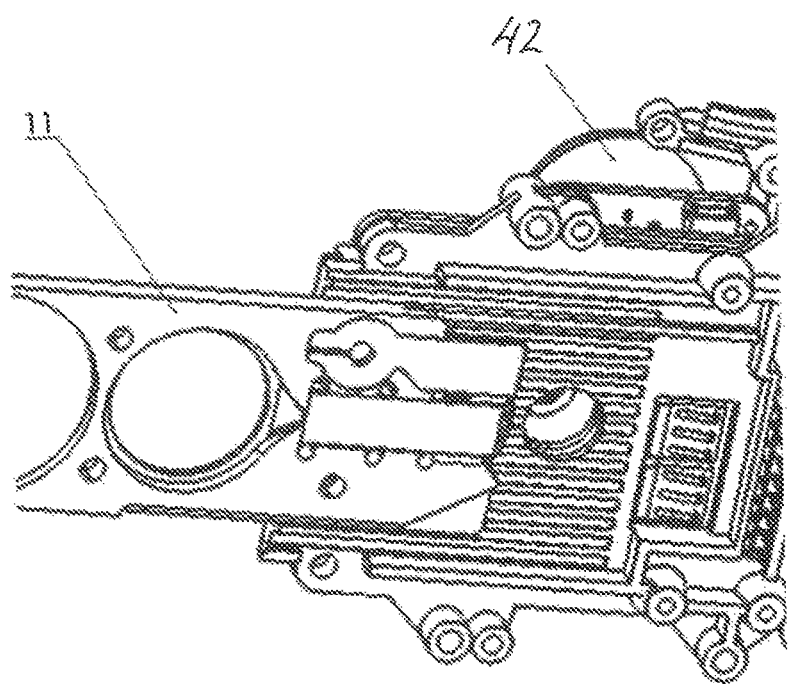
FIGS. 7a, 7b illustrate a cartridge holder and cartridge for use within a device.
Figure 7B:
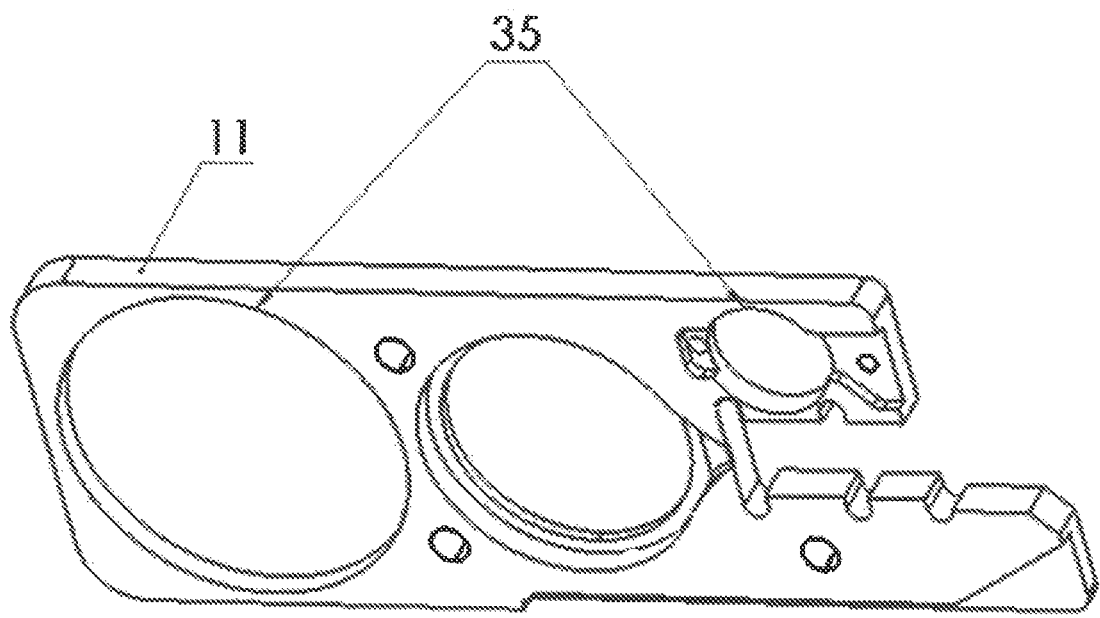

A cartridge 11, shown in FIGS. 7a, 7b, is located in the vicinity of the breath inlet 31. The cartridge 11 includes, amongst other things, RFID tags 35 which can be used to ensure firstly that correct logging of the cartridge 11 is made and can be linked to the user. Additionally, the tags 35 enable the age of a cartridge to be checked so that it can be determined whether a cartridge is still within date. The cartridge 11 also typically comprises a microfluidic array, including sensors and reagents associated therewith to enable the determination of various parameters and analytes. Such arrays are known in the art and would be available to the skilled person.

Within the device 30 is an accelerometer 36 which has a number of functions. First, the accelerometer 36 can determine that the device 30 is being held in the correct orientation. Secondly, the accelerometer 36 allows a determination of any movement of the device 30 whilst in use. This can show for example whether a user's hand is shaking, which may be detrimental to the flow of fluid within the device 30 and lead to erroneous results.

The location of the $CO_2$ sensor 42 is shown, along with a further sensor 43. In the embodiment of the device 30 the breath to the $CO_2$ sensor 42 flows along a tube 44 (shown in FIG. 4) located on the outside of the device 30. The sensor 43 is similarly fed by another, separate, tube. A further set of sensors is located on the in-use lower portion 37 of a pcb card 38 housing a temperature and relative humidity sensor as well as a 3-axis accelerometer sensor.

In FIG. 6, the condenser plate 45 is shown directly behind the cartridge 11. A Peltier piece 46 is housed adjacent the plate 45 to provide cooling thereto when required. Power for the Peltier piece 46 and other components of the device is provided by a battery 47.

Information obtained through the sensors can be passed through a USB interface 48 to an outside monitoring system. Processing of data can be carried out externally or also on a further pcb 49 mounted within the device 30. In order to provide information to a user via the hand-held device 30, a user interface 149 is also provided. Further information such as on $H_2O_2$ levels can be obtained via a connection point 80 which can also be used to determine and relay as to whether a valid cartridge 11 is present. Should it be desirable to remove $H_2O_2$ from atmosphere breathed by the user, then a filter can be fitted at the air inlet. In order to draw air through the device 30 where required a fan 81 is included which can draw power from the battery 47.

Figure 8:
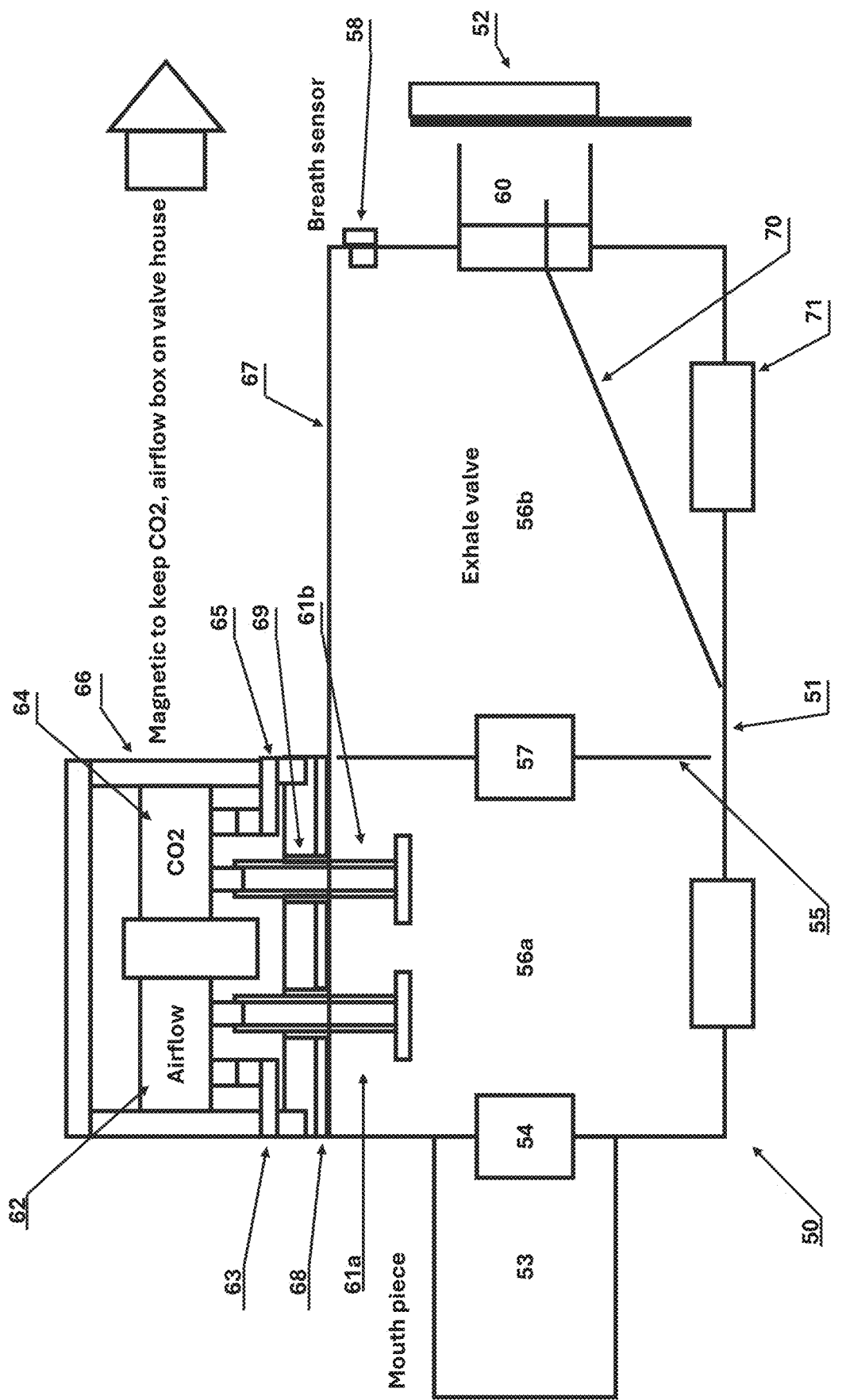
FIG. 8 is an illustration of breath flow within a device.
Figure 9:
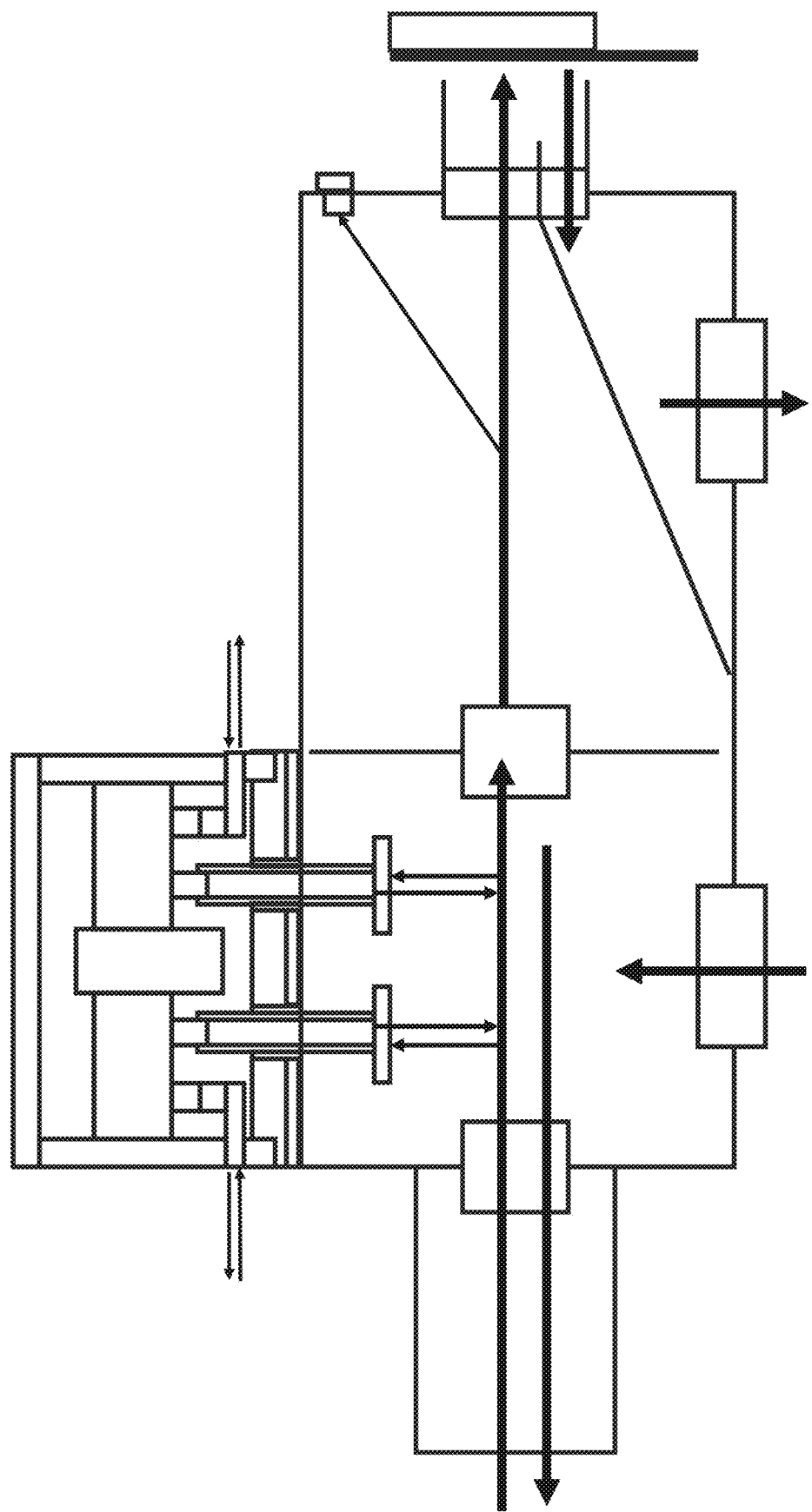
FIG. 9 is a further illustration of breath flow within a device.
Figure 10A:
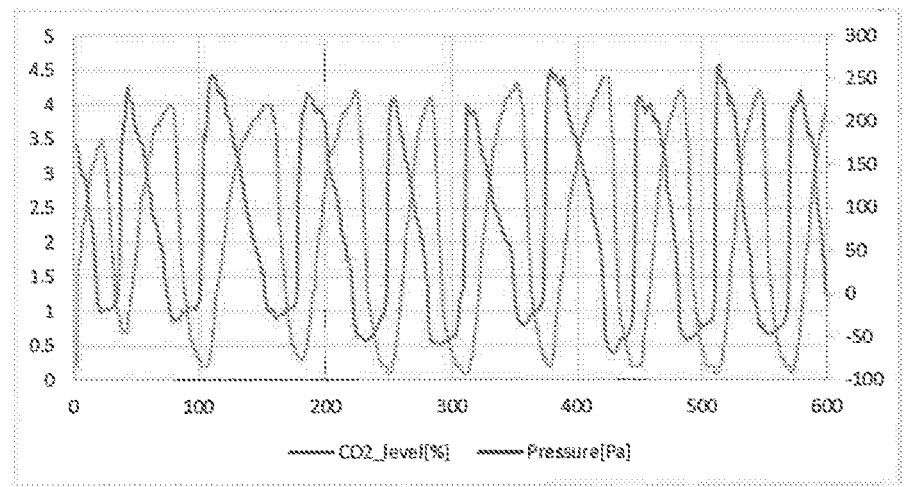
FIG. 10a, 10b are graphical representations of measured parameters of exhaled breath.
Figure 10B:
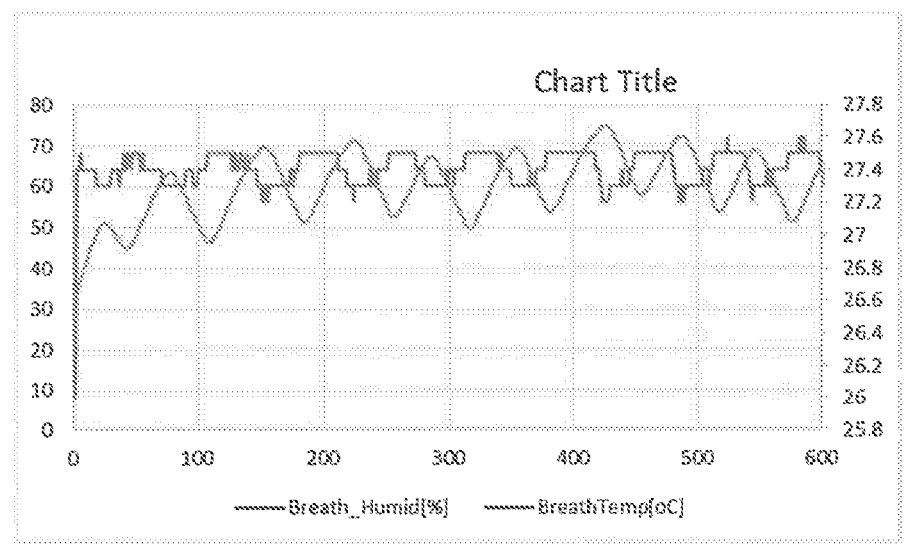

Turning now to FIGS. 8 and 9, these illustrate diagrammatically a device in accordance with the invention. In FIG. 8, component elements of a device 50 are shown. FIG. 9 shows airflow through the device of FIG. 8. The device 50 has a primary body 51, substantially tubular in form. The body 51 enables exhaled air from a user, entering the body 51 at one end to be guided to a condenser plate 52 at the other end. Therebetween, flow is controlled to allow a user to inhale whilst using the device 50 and also enabling analysis of the breath to be carried out.

In more detail, fixed to one end of the body 51 is a mouthpiece 53. The mouthpiece 53 can be detachably mounted to the body 51 to allow, following cleaning of the rest of the device 50, attachment of a further mouthpiece to enable another user to use the device 50. The mouthpiece 53 is fluidly connected to the internal volume of the body 51 by means of a two-way valve 54. The body 51 is divided by a chamber wall 55 into 2 chambers 56a, 56b. The first chamber 56a is linked to the mouthpiece 53 via the valve 54. The second chamber 56b is fluidly linked via a one-way valve 57 to the first chamber 56a, the valve allowing flow from the first to the second chamber. The chamber wall 55 and the means of allowing a portion of the breath to pass from the first to the second chamber acts to prevent unwanted fractions of the exhaled breath from reaching the condenser plate 52. The chamber wall 55 enables the first chamber 56a to function to allow air to be drawn into the body 51 without affecting the passage of breath to the breath sensor 58 and condenser plate 52 associated with the second chamber 56b. Additionally, the chamber wall 55 acts to cause a degree of turbulent flow within the first chamber. This acts to limit the Bernoulli effect on air-flow within the sensors 62, 64 (see below) which might otherwise cause air to flow from these sensors 62, 64 into the first chamber 56a rather than through the sensors 62, 64.

The sensor 58 provides data on several parameters. For example, the sensor 58 can include a relative humidity (RH) sensor and a temperature sensor. The majority of the airflow entering the second chamber 56b exits onto the condenser plate 52 via the aperture 60. The condenser plate 52 is maintained cold to condense out the aqueous component of the breath along with other materials dissolved therein. Liquid condensing on the condenser plate 52 can then be led away for analysis in a suitably arranged microfluidic array. In order to better focus flow of breath onto the condenser plate 52, a sloping internal wall 70 is provided. Additionally, a one-way exit valve 71 allows, in effect, pressure from rebounding breath off the condenser plate 52, to flow out of the device 50, rather than back into the second chamber 56b, where it would cause turbulent flow with any incoming breath. Such turbulent flow would affect results obtained, not least because of the chaotic flow conditions caused.

Further fluid outlets in the body 51 allow breath to be led to further analysers located externally of the body 51. The first further outlet 61a directs exhaled breath into an airflow measuring sensor 62. The data from the airflow measuring sensor enables a determination as to whether the user is correctly using the device 50 and also gives an indication of the overall effectiveness of the user's lungs. A typical airflow measuring sensor includes a piezo-electric element which becomes deformed due to the pressure of the airflow with a one-to-one link between said pressure and the deformation caused in the piezo-electric element. A fluid path out of the sensor 62 is provided by the tube 63. The second further outlet 61b leads to a $CO_2$ sensor 64. As an example of a $CO_2$ sensor 64 is a near-infrared detector. Again, a tube 65 is provided to supply a fluid path out of the sensor 64.

Both the airflow measuring device 62 and the $CO_2$ sensor 64 are retained within a housing 66. The housing 66 is demountably mounted to the outside of the body 51, with the outlets 61a, 61b extending through the wall 67 of the body 51. In the illustrated embodiment shown, a steel plate 68 is secured to the wall 67. Magnets 69 are then utilised to hold the housing 66 magnetically against the plate 68. It will be recognised that other means of fixing the housing 66 to the body 51, known in the art, can be used.

The device should have at least one measurement point for the breath humidity located upstream of any scrubbers, condensers, dehumidifiers, driers etc., which may also be present within the device.

The use of valves and controlled volumes within the device should be configured to give a certainty that the sample being measured is the result of exhaled breathing and not a mixture of breath and ambient air. Clearly contaminant such as saliva carried from the mouth in the form of aerosol should be prevented from reaching the sensor and contaminating the sensor.

Measurements made on the breath are currently used in the identification of disease such as COPD and Asthma, herein is described a device for measuring the humidity of the breath, the clinical use of such a measurement and the use of breath humidity alongside a number of parameters measured on the breath.

A device for measuring the breath humidity must be able to engage with the patient's mouth. Those parts of the device which make contact with the mouth must be able to be readily decontaminated between patients, or preferably disposed of to eliminate the risk of cross-contamination. The device optionally has a means by which to trap saliva so as to prevent aerosol and particulates from the mouth making their way into the body of the device or risk contaminating the humidity sensor. The device should preferably allow the patient to inhale but have an internal volume less than the expected tidal breathing exhalation volume which is typically approximately 500 $cm^3$, so the exhaled breath dominates the internal volume of the device. The device should be able to measure breath humidity, as well as preferably breath temperature and ideally breath relative humidity. The device should optionally measure the exhaled breath pressure, flow rate and carbon dioxide levels. The device should be able to measure all parameters as a function of time so that parameters such as carbon dioxide, breath inhalation/exhalation pressure, carbon dioxide concentration, breath temperature, breath humidity, breath relative humidity, ambient humidity, ambient relative humidity, ambient temperature etc. can all be temporally aligned and compared. The device can optionally have additional functions such as the condensation and analysis of exhaled breath, the removal of breath vapour, the measurement of gas phase molecules including FNO.

In applications where the removal or collection of breath vapour is important a second humidity sensor can be positioned downstream of the initial breath humidity sensor and the vapour collection point so as to measure the breath humidity post vapour collections. The difference between the breath humidity sensors and the post vapour collection sensors allows for a determination of the collected volume of vapour and the efficiency of the collection.

The invention claimed is:

1. A device to measure breath humidity, the device comprising:
   a tubular body, said tubular body defining an inner tube volume and having a first end, a second end, and a tubular body wall,
   an inlet fluidly connected to the inner tube volume,
   a condenser plate, fluidly connected to the second end of the tubular body to receive exhaled breath;
   a partition wall intermediate the first end and the second ends and dividing the inner tube volume into a first chamber and a second chambers, the second chamber providing fluid access to the condenser plate;
   wherein the partition wall has a one-way valve therethrough allowing the breath to travel from the first chamber to the second chamber;
   one or more apertures in the tubular body wall of the first chamber, wherein each of the one or more apertures fluidly link a sensor to the first chamber,
   a relative humidity sensor fluidly linked to the second chamber;
   a processor, said processor receiving data from the relative humidity sensor and the sensor, and processing the data to derive a combined Helle Score.

2. The device according to claim 1, wherein the sensor is linked to a data storage device.

3. The device according to claim 1, wherein the sensor is a $CO_2$ sensor.

4. The device according to claim 1, wherein the sensor is an air-flow sensor.

5. The device according to claim 1, wherein the sensor is a hydrogen peroxide sensor.

6. The device according to claim 1, wherein the sensor is housed in a demountable housing, attachable to the device.

7. The device according to claim 1, wherein the device includes a Peltier piece type cooling means to cool the condenser plate.

8. The device according to claim 7, wherein a heater plate is housed in cooling arrangement with the Peltier piece type cooling means.

9. The device according to claim 8, wherein the device includes a fan arranged to draw air across the heater plate.

10. The device according to claim 1, wherein the device includes an accelerometer.

11. The device according to claim 1, wherein the second chamber has a fluid outlet to discharge the breath from the device.

12. The device according to claim 1, wherein the second chamber includes a directing means.

13. The device according to claim 12, wherein the directing means is a ramp.

* * * * *